United States Patent
Murali et al.

(10) Patent No.: US 10,831,266 B2
(45) Date of Patent: Nov. 10, 2020

(54) PERSONALIZED ADAPTATION OF VIRTUAL REALITY CONTENT BASED ON EYE STRAIN CONTEXT

(71) Applicant: International Business Machines Corporation, Armonk, NY (US)

(72) Inventors: Srikanth K. Murali, Bangalore (IN); Vijay Kumar Ananthapur Bache, Bangalore (IN); Vijay Ekambaram, Tamilnadu (IN); Padmanabha Venkatagiri Seshadri, Mysore (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/239,377

(22) Filed: Jan. 3, 2019

(65) Prior Publication Data

US 2020/0218342 A1 Jul. 9, 2020

(51) Int. Cl.
*G06F 3/01* (2006.01)
*G02B 27/01* (2006.01)
*G06T 19/00* (2011.01)
*A61B 3/00* (2006.01)

(52) U.S. Cl.
CPC ............ *G06F 3/013* (2013.01); *A61B 3/0025* (2013.01); *G02B 27/017* (2013.01); *G06T 19/003* (2013.01)

(58) Field of Classification Search
CPC .................................................. G06T 7/246
See application file for complete search history.

(56) References Cited

U.S. PATENT DOCUMENTS

| 6,389,437 B2 | 5/2002 | Stoub |
| 8,749,737 B2 | 6/2014 | Chen et al. |
| 8,860,653 B2 | 10/2014 | Mahowald et al. |

(Continued)

FOREIGN PATENT DOCUMENTS

| CN | 104503683 | 4/2015 |
| WO | 2011127689 | 10/2011 |

OTHER PUBLICATIONS

"Oculus Rift Oculus Support Center" (online) retrieved from the Internet on Mar. 4, 2019 at URL>https://support.oculus.com/rift/, Total 1 page.

(Continued)

*Primary Examiner* — Cao H Nguyen
(74) *Attorney, Agent, or Firm* — Janaki K. Davda; Konrad, Raynes, Davda and Victor LLP

(57) ABSTRACT

Provided are techniques for personalized adaptation of Virtual Reality (VR) content based on eye strain context. An initial eye strain context for a user while wearing a VR headset to view VR content in a User Interface (UI) is determined. A UI adaptation and an intensity of the UI adaptation is identified, where the UI adaptation is any one of an object velocity back and forth adaptation, a rotation movement calibration adaptation, and an object position adaptation. Modified VR content is rendered in the UI by applying the UI adaptation based on the intensity of the UI adaptation. An updated eye strain context is determined. In response to determining that the updated eye strain context indicates that eye strain has decreased, a priority weight for the UI adaptation is increased and the UI adaptation, the intensity of the UI adaptation, and the priority weight are saved in a user profile.

18 Claims, 8 Drawing Sheets

(56) References Cited

U.S. PATENT DOCUMENTS

| | | | |
|---|---|---|---|
| 9,125,274 | B1 | 9/2015 | Brunault et al. |
| 9,183,806 | B2 | 11/2015 | Felt |
| 9,183,812 | B2 | 11/2015 | Myers et al. |
| 9,262,690 | B2 | 2/2016 | Chiu |
| 9,373,177 | B2 | 6/2016 | Tucker et al. |
| 9,478,173 | B2 | 10/2016 | Safaee-Rad et al. |
| 9,841,811 | B2 | 12/2017 | Reiner |
| 2006/0274197 | A1 | 12/2006 | Yoo |
| 2012/0068998 | A1 | 3/2012 | Hong |
| 2013/0044291 | A1 | 2/2013 | Kato et al. |
| 2014/0347265 | A1* | 11/2014 | Aimone ............ A61B 5/04842 345/156 |
| 2016/0140889 | A1 | 5/2016 | Wu et al. |
| 2016/0232715 | A1* | 8/2016 | Lee ....................... G06T 19/006 |
| 2017/0127055 | A1 | 5/2017 | Khabiri et al. |
| 2017/0160798 | A1* | 6/2017 | Lanman .................. G06T 5/002 |
| 2019/0045125 | A1* | 2/2019 | Jarvenpaa ............... G06T 7/246 |
| 2019/0265785 | A1* | 8/2019 | Ho .......................... G09G 3/20 |

OTHER PUBLICATIONS

"You Haven't Seen It Until You Seen it in VR", (online) retrieved from the Internet on Mar. 4, 2019 at URL> https://www.oculus.com/, Total 6 pages.

R. Mukamal, "Are Virtual Headsets Safe for Eyes?" (online), Feb. 28, 2017, Retrieved from the Internet at URL>https://www.aao.org/eye-health/tips-prevention/are-virtual-reality-headse . . . , 4 pages.

E. Stinson, "How to Reduce VR Sickness? Just Add A Virtual Nose", dated Apr. 20, 2015, (online) Retrieved from the Internet at URL>https://www.wired.com/2015/04/reduce-vr-sickness-just-add-virtual-nose/, 8 pages.

"Virtual Reality: Vision Concerns and VR Technology" dated 2015, (online) Retrieved from the Internet at URL>http://www.trinityeyecare.com/vision-concerns-vr-technology/, 3 pages.

J. Erbentraut "Glimpsing The Virtual Reality Future Of How We Treat Eye Problems" dated Aug. 29, 2015, (online), retrieved from the Internet at URL>https://www.huffingtonpost.in/entry/virtual-reality-headsets-vision-problems_us_55df6169 . . . , 5 pages.

M. Munda "Afraid of Getting Sick in VR? You Shouldn't Be!Heres How To Avoid It!" dated Mar. 9, 2017, (online) Retrieved from the Internet at URL>https://www.viarbox.com/single-post/vr-myths, 3 pages.

R. Menon, "The Side Effects of Virtual Reality And How They Can Be Fixed" dated Jun. 16, 2016, (online) http://www.travancoreanalytics.com/side-effects-of-virtual-reality-how-they-can-be-fixed, 3 pages.

"This is How Virtual Reality Could Go Spectacularly Wrong" (online), Retrieved from the Internet on Nov. 30, 2018 at URL>http://www.zdnet.com/pictures/this-is-how-virtual-reality-could-go-spectacularly-wrong/2/, 5 pages.

N. Padmanadan et al., "Optimizing Virtual Reality For All Users Through Gage-Contingent And Adaptive Focus Displays" dated Feb. 28, 2017, vol. 114, 4 pages.

V. Ramachandran, "Stanford Researchers Personalize Virtual Reality Displays to Match A User's Eyesight" dated Feb. 13, 2017, (online) https://news.stanford.edu/press-releases/2017/02/13/personalized-virs-m . . . , 3 pages.

L. Leroy, et al., "Visual Fatigue Reduction for Immersive Stereoscopic Displays by Disparity, Content, and Focus-Point Adapted Blur" (online) https://ieeexplore.ieee.org/document/6041027?anchor=authors, 2 pages.

C. Pruett, "Lessons From the Frontiers: Modern VR Design Patterns", dated Jun. 9, 2017, (online) retrieved from the Internet at URL>https://developer.oculus.com/blog/lessons-from-the-frontlines-modern-vr-design-patterns/, 12 pages.

B. Riecke et al., "Scene Consistency and Spatial Presence Increase the Sensation of Self-Motion in Virtual Reality" dated 2005, 8 pages.

H. Distler et al., "Velocity Constancy In A Virtual Reality Environment", dated 2000, vol. 29, 14 pages.

S. Lavalle "Virtual Reality" dated 2017, Cambridge University Press, (online) retrieved from the Internet at URL>http://vr.cs.uiuc.edu/vrbook.pdf , 24 pages.

A. Dahl, "Eye Strain", (online) retrieved from the Internet on Nov. 30, 2018, at URL>https://www.medicinenet.com/eye_strain/article.htm#eye_strain _facts, 3 pages.

"Yoga for Eyes—Improve Eyesight Naturally" (online) retrieved from the Internet on Nov. 30, 2018 at URL>https://www.artofliving.org/in-en/yoga/health-and-wellness/yoga-eyes, 11 pages.

"Dark or White Color Theme is Better for the Eyes? [duplicate]" dated Mar. 4, 2017, (online) , retrieved from the Internet at URL>https://ux.stackexchange.com/questions/53264/dark-or-white-color-theme- . . . , 1 page.

J. Sheedy et al., "Blink: The Stress of Reading", dated 2008, (online), retrieved from the Internet at URL>http://www.eyemagazine.com/opinion/article/eye-strain, 3 pages.

S. Han et al., "EyeGuardian: A Framework of Eye Tracking and Blink Detection for Mobile Device Users", dated 2012, in Proceedings of the Twelfth Workshop on Mobile Computing Systems & Applications (HotMobile '12). ACM, New York, NY, USA, Article 6, 6 pages.

B. Anand et al., "El-pincel: A Painter Cloud Service for Greener Web Pages", dated 2012, in Proceedings of the 20th ACM international conference on Multimedia (MM '12). ACM,10 pages.

R. Raskar et al., "Glare Aware Photography: 4D Ray Sampling for Reducing Glare Effects of Camera Lenses" In ACM SIGGRAPH 2008 papers (SIGGRAPH '08). ACM, New York, NY, USA, Article 56 , 12 pages.

O. Yilmaz et al., "Detection and Localization of Specular Surfaces Using Image Motion Cues", dated 2014, . Mach. Vision Appl. 25, 5 (Jul. 2014), 16 pages.

A. Plopski et al., "Hybrid Eye Tracking: Combining Iris Contour and Corneal Imaging", dated 2015, In Proceedings of the 25th International Conference on Artificial Reality and Telexistence and 20th Eurographics Symposium on Virtual Environments (ICAT-EGVE '15), 8 pages.

B. Anand et al., "Adaptive Display Power Management for Mobile Games", dated 2011, In Proceedings of the 9th International Conference on Mobile Systems, Applications, and Services (MobiSys '11), 14 pages.

H. Han et al., "E3: Energy-Efficient Engine for Frame Rate Adaptation on Smartphones" dated 2013, In Proceedings of the 11th ACM Conference on Embedded Networked Sensor Systems (SenSys '13), ACM, 14 pages.

M. Dong et al., "Chameleon: A Color-Adaptive Web Browser for Mobile OLED Displays", dated 2010-2012, Also In Proceedings of the 9th International Conference On Mobile Systems, Applications, and Services (MobiSys '11), ACM, 14 pages.

X. Chen et al., "FingerShadow: An OLED Power Optimization Based on Smartphone Touch Interactions", dated 2014, In Proceedings of the 6th USENIX conference on Power-Aware Computing and Systems (HotPower'14), 5 pages.

D. Raneburger et al., "A User Study with GUIs Tailored for Smartphones", dated 2013, 14th International Conference on Human-Computer Interaction, Total 9 pages.

A. Shafiei et al., "Jiku Live: A Live Zoomable Video Streaming System", dated 2012, Department of Computer Science National University of Singapore, Total 2 pages.

Heath et al., "Image Webs: Computing and Exploiting Connectivity In Image Collections" dated 2010, In Computer Vision and Pattern Recognition (CVPR), 2010 IEEE Conference on, pp. 3432-3439. IEEE, 2010, 24 pages.

N. Mezhoudi, "User Interface Adaptation Based on User Feedback and Machine Learning" dated 2013, In Proceedings of the Companion Publication of the 2013 International Conference on Intelligent User Interfaces Companion (IUI '13 Companion) 4 pages.

M. Constantinides "Apps with Habits: Adaptive Interfaces for News Apps", dated 2015, In Proceedings of the 33rd Annual ACM Conference Extended Abstracts on Human Factors in Computing Systems(CHI EA '15). ACM, 4 pages.

R. Wang et al., "Using Opportunistic Face Logging From Smartphone to Infer Mental Health: Challenges and Future Directions", dated 2015, In Adjunct Proceedings of the 2015 ACM International Joint

(56) References Cited

OTHER PUBLICATIONS

Conference on Pervasive and Ubiquitous Computing and Proceedings of the 2015 ACM International Symposium on Wearable Computers (UbiComp/ISWC'15 Adjunct), 10 pages.

Jabon et al., "Facial Expression Analysis for Predicting Unsafe Driving Behavior." dated 2009, Traffic 1 (also IEEE 2011), 12 pages.

Gao et al., "Detecting Emotional Stress from Facial Expressions for Driving Safety." dated 2014, IEEE International Conference on Image Processing (ICIP), pp. 5961-5965. IEEE, 2014, 5 pages.

WO 2011127689, Oct. 20, 2011, is submitted for PCT/CN2010/074254.

CN104503683, Apr. 8, 2015, is submitted for CN201410714869.

\* cited by examiner

PERSONALIZED ADAPTATION OF VIRTUAL REALITY CONTENT BASED ON EYE STRAIN CONTEXT

BACKGROUND

1. Field of the Invention

Embodiments of the invention relate to personalized adaptation of Virtual Reality (VR) content based on eye strain context.

2. Description of the Related Art

A VR headset may be described as a device that may be mounted on a person's head and covers a person's eyes. The VR headset may be used for games, simulator, trainers, etc. The VR headset may provide separate images for each eye, stereo sound, and head motion tracking sensors They comprise a stereoscopic head-mounted display (providing separate images for each eye), stereo sound, and head motion tracking sensors (to allow for shifting the picture as the head moves).

The VR headset creates a life-size, three-dimensional (3D) virtual environment and enable perception of depth and an increased field of view (width of the picture) to create a sense of immersion.

Each year a new toy emerges on the market challenging the newest technology and expectations. Even though VR technology is still developing, there are concerns over its long term effects on user's eyesight.

The simplest way to use VR technology is through head mounted displays (HMD's). With a host of new games, apps and headsets offering an engaging 3D experience for users, it's not surprising that many families are embracing VR technology.

However, continuous usage of VR headsets (i.e., long viewing of VR content) may lead to eye stress, dizziness, motion sickness. Other problems may occur with eye dryness/focus/movement, headaches, convergence accommodation conflicts, and coordination imbalance. Some VR headsets come with disclaimers stating that children under the age of 13 should not use their headsets because prolonged use may negatively impact hand-eye coordination, balance, and multi-tasking ability.

Some conventional solutions address eye tracking for medical purposes, color setting, ambient light sensing, adapting data, power efficiency, reducing backlight, color tuning, reduced frame rate during scrolling, finger shadows, network efficiency, and feed-back based adaptation.

SUMMARY

In accordance with embodiments, a computer-implemented method is provided for personalized adaptation of VR content based on eye strain context. An initial eye strain context for a user while wearing a Virtual Reality (VR) headset to view VR content in a User Interface (UI) is determined. A UI adaptation and an intensity of the UI adaptation is identified, where the UI adaptation is any one of an object velocity back and forth adaptation, a rotation movement calibration adaptation, and an object position adaptation. Modified VR content is rendered in the UI by applying the UI adaptation based on the intensity of the UI adaptation. An updated eye strain context is determined. In response to determining that the updated eye strain context indicates that eye strain has decreased, a priority weight for the UI adaptation is increased and the UI adaptation, the intensity of the UI adaptation, and the priority weight are saved in a user profile for the user.

In accordance with other embodiments, a computer program product is provided for personalized adaptation of VR content based on eye strain context. The computer program product comprising a computer readable storage medium having program code embodied therewith, the program code executable by at least one processor to perform operations. An initial eye strain context for a user while wearing a Virtual Reality (VR) headset to view VR content in a User Interface (UI) is determined. A UI adaptation and an intensity of the UI adaptation is identified, where the UI adaptation is any one of an object velocity back and forth adaptation, a rotation movement calibration adaptation, and an object position adaptation. Modified VR content is rendered in the UI by applying the UI adaptation based on the intensity of the UI adaptation. An updated eye strain context is determined. In response to determining that the updated eye strain context indicates that eye strain has decreased, a priority weight for the UI adaptation is increased and the UI adaptation, the intensity of the UI adaptation, and the priority weight are saved in a user profile for the user.

In yet other embodiments, a computer system is provided for personalized adaptation of VR content based on eye strain context. The computer system comprises one or more processors, one or more computer-readable memories and one or more computer-readable, tangible storage devices; and program instructions, stored on at least one of the one or more computer-readable, tangible storage devices for execution by at least one of the one or more processors via at least one of the one or more memories, to perform operations. An initial eye strain context for a user while wearing a Virtual Reality (VR) headset to view VR content in a User Interface (UI) is determined. A UI adaptation and an intensity of the UI adaptation is identified, where the UI adaptation is any one of an object velocity back and forth adaptation, a rotation movement calibration adaptation, and an object position adaptation. Modified VR content is rendered in the UI by applying the UI adaptation based on the intensity of the UI adaptation. An updated eye strain context is determined. In response to determining that the updated eye strain context indicates that eye strain has decreased, a priority weight for the UI adaptation is increased and the UI adaptation, the intensity of the UI adaptation, and the priority weight are saved in a user profile for the user.

BRIEF DESCRIPTION OF THE SEVERAL VIEWS OF THE DRAWINGS

Referring now to the drawings in which like reference numbers represent corresponding parts throughout.

DETAILED DESCRIPTION

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Embodiments enable VR content to auto-adapt to avoid eye fatigue in users (wearers of the VR headset). Embodiments re-represent the VR content in a different User Interface (UI) form to suit the energy needs of the VR headset. Embodiments adapt the UI by considering user feedback, which helps cater to the aesthetics of the UI while also trying to achieve energy/network efficiency. Embodiments incorporate direct and indirect feedback to balance user comfort and energy efficiency.

Figure 1:
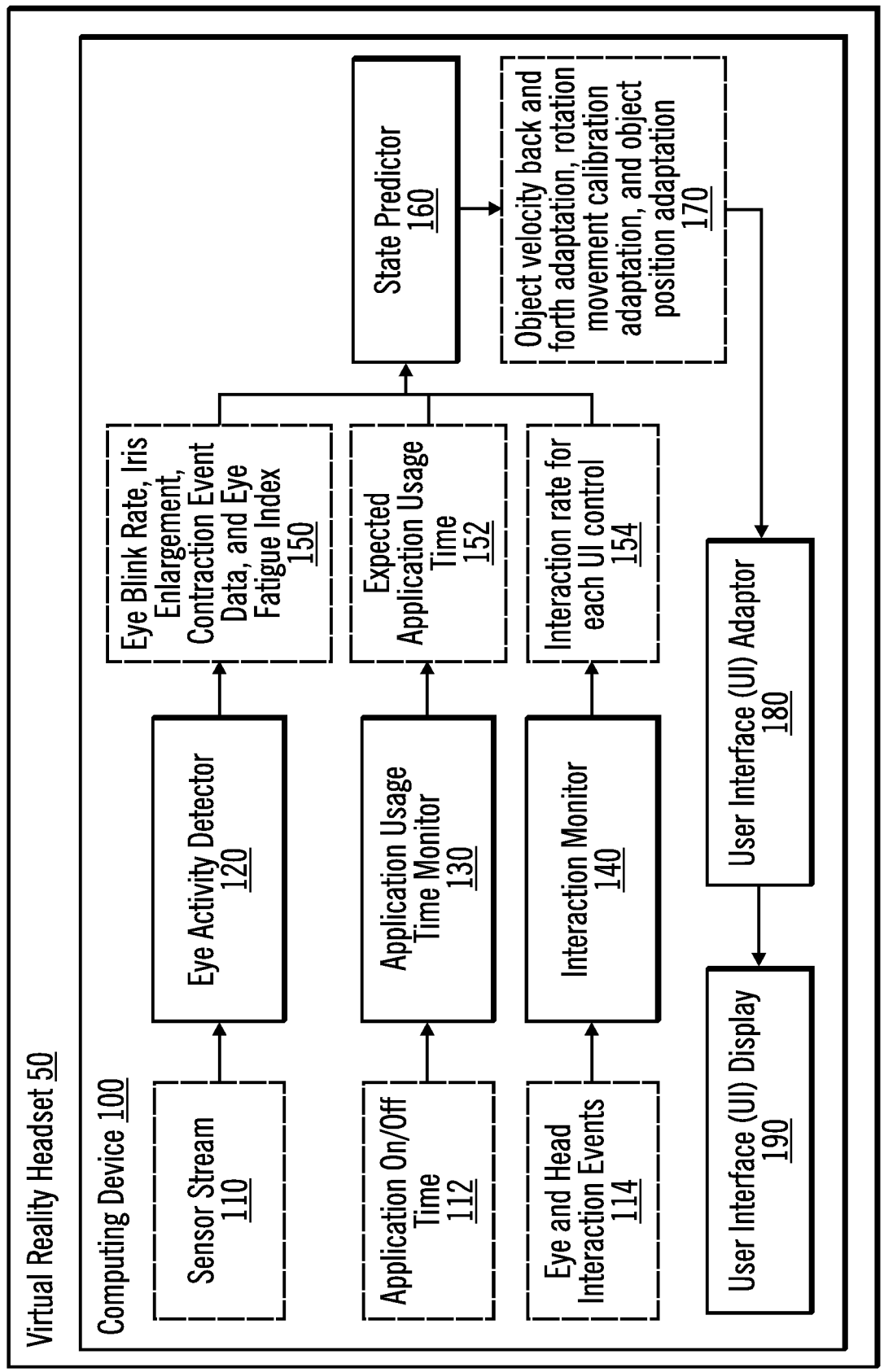
FIG. 1 illustrates, in a block diagram, a computing environment of a VR headset in accordance with certain embodiments.

FIG. 1 illustrates, in a block diagram, a computing environment of a VR headset 50 in accordance with certain embodiments. The VR headset 50 includes a computing device 100. The computing device 100 includes an eye activity detector 120, an application usage time monitor 130, an interaction monitor 140, a stat predictor 160, a UI adaptor 180, and a UI display 190. The UI 190 displays one or more objects for viewing by the user of the VR headset.

The VR headset 50 may include sensors or may receive sensor data from sensors apart from the VR headset 50. The sensor data forms a sensor stream 110 that is input to an eye activity detector 120. The eye activity detector 120 processes the sensor stream 110 to output eye blink rate, iris enlargement, contraction event data, and an eye fatigue index 150.

The application usage time monitor 130 receives as input the application on/off time 112 as input and outputs an expected application usage time 152.

The interaction monitor 140 receives as input eye and head interaction events 114 (i.e., movements of the eye and head of the user) and outputs an interaction rate for each UI control 154. In certain embodiments, the UI controls 154 may be described as application widgets.

The state predictor 160 receives as input the eye blink rate, iris enlargement, contraction event data, and an eye fatigue index 150, the expected application usage time 152, and the interaction rate for each UI control 154. Using these inputs, the state predictor 160 outputs an object velocity back and forth adaptation, a rotation movement calibration adaptation, and an object position adaptation 170 for one or more of the objects in the UI.

The UI adaptor 180 receives the velocity, the rotation movement calibration, and the position adaptation at an object level 170 and modifies the UI displayed by the UI display 190.

The UI adaptor 180 personalizes and adapts the user interface of VR content (e.g., VR games) by tracking the continuous feedback from a VR user's eye strain context. Eye strain context may be any one or more of the following states (but not limited to): rapid eye focus change, more extreme corner eye movements, static long-time same eye-focus, less eye-blinking, and eye tears and tiredness.

In different embodiments, different techniques may be used to detect eye-strain context. In certain embodiments, the UI adaptor 180 detects eye strain context by deriving an eye fatigue index and then determining the eye strain context. In certain embodiments, the eye fatigue index is derived by the eye activity detector 120 using sensors in the VR headset by tracking eye blink rate, iris enlargement/iris focus change, eye trajectory movements, and ambient lightening. In certain embodiments, the VR headset includes an optical sensor and a camera, which tracks eye movements and other inferences to derive the eye fatigue index. Based on these inputs and correlating these with vision do's and don'ts principles, the UI adaptor 180 determines an eye strain context of the user. Since the VR head-set is very close to the eyes, these inputs may be derived accurately.

The eye strain context is provided as continuous feedback to the UI adaptor 180 of the VR headset 50. The UI adaptor 180 renders the VR content and may include a rendering engine. The UI adaptor 180 adapts and personalizes the adaptation of velocity, rotation movement calibration, and positions of various objects in the VR space based on the eye fatigue index.

When eye strain is not detected, the UI adaptor 180 renders the original VR content, without modification (e.g., to allow players of a VR game to enjoy the full user experience). However, when eye-strain is detected, the UI adaptor 180 adapts and renders the VR content by making one or more of the following UI adaptations: object velocity back and forth adaptation, rotation movement calibration adaptation, and object position adaptation. Additionally, the UI adaptor 180 changes the intensity of the UI adaptations based on the intensity of the eye strain.

In certain embodiments, for object velocity back and forth adaptation, when objects move back (e.g., away from the user) and forth (e.g., forwards towards the user) from user eyes at a high rate of speed, the user eye focus rapidly changes, leading to eye strain. So, when eye-strain is detected, the UI adaptor 180 scales down the object velocity and the same experience is rendered through other artifacts. The other artifacts may include: more vibration in movement (which makes the object movement appear faster to the user), an increase in pauses in objects between object direction changes, a change in color of objects, etc. The object velocity back and forth adaptation may also be referred to as object velocity to and from adaptation. Thus, the object velocity back and forth adaptation decreases a velocity of an object in the VR content and adds another artifact.

In certain embodiments, for rotation movement calibration adaptation (with regard to horizontal and vertical extreme), a user may find difficulties in viewing objects in extreme corners (i.e. left/right/top/bottom most) as it leads to more movement of eyes and/or the head towards corners, which could lead to eye stress if head rotations are not noticed. In these cases, the UI adaptor 180 increases the rotation calibration index, which results in the user moving slightly, which may lead to high magnitude of rotation. In certain embodiments, the rotation calibration index is a scaling number. When eye strain is higher, then the rotation calibration index (scale value) is higher. For example, when the user moves the head slightly, the VR environment rotates more based on the scaling value.

In certain embodiments, for object position adaption, when user focus is more static in a defined area, it may lead to eye stress due to same point focus issues. So, in these contexts, the UI adaptor 180 places user interaction widgets widely apart, leading the user to more eye wandering in the VR space, which avoids same area focus issues.

With embodiments, these adaptations by the UI adaptor 180 may be made more personalized by capturing the eye fatigue index after adaption and deriving a user-acceptance score for every adaption. Based on the user-acceptance score, personalization happens. In certain embodiments, the eye fatigue index is derived using the optical sensor and the camera of the VR headset. In certain embodiments, the user-acceptance score is derived by the state predictor 160 based on a detected reduction in eye strain. In alternative embodiments, the user-acceptance score may be based on user feedback.

With embodiments, the UI adaptor 180 determines eye strain context of the user and enables personalized adaptation of object velocity, rotation movement calibration, and object position of various objects in the VR space. Adaptation not only refers to avoiding/removing the object behavior that leads to eye-strain, but rendering the same experience using other modalities or forms. Thus, the user views the complete user experience, while avoiding or limiting eye strain. Due to continuous feedback, when the user has eye strain, the UI adaptor 180 identifies the context of the eye-strain and adapts the UI in a different form so that user doesn't lose the user experience and at the same time avoids eye strain (to protect their eyes). These UI adaptor 180 may roll back the adaptations to display the original VR content when the UI adaptor 180 determines that eye-strain is reduced.

Figure 2:
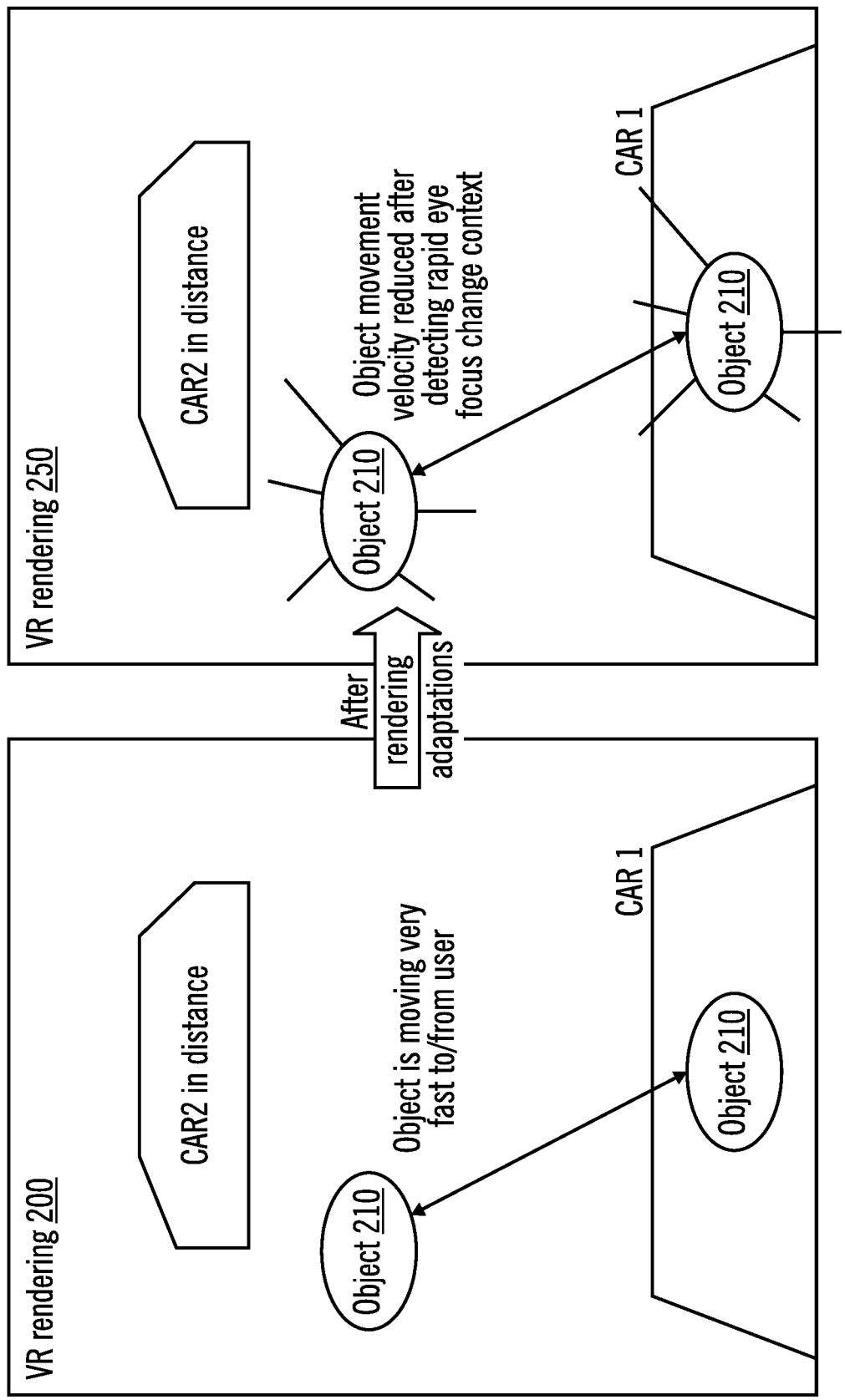
FIG. 2 illustrates object velocity back and forth adaptation in accordance with certain embodiments.

FIG. 2 illustrates object velocity back and forth adaptation in accordance with certain embodiments. Rendering 200 illustrates the VR content before adaptation. Rendering 200 includes an object 210 moving very fast to and from the user. Rendering 250 illustrates the VR content after adaptation. In rendering 250, the UI adaptor 180 reduces movement velocity of the object 200 after detecting rapid eye focus change context, but modifies the object 210 to add spikes.

When objects move back and form from the user's eyes at a high rate of speed, the user's eye focus rapidly changes, which leads to eye strain. When such eye-strain is detected, the UI adaptor 180 scales down (slows down) object velocity and the same experience is rendered through other artifacts.

Figure 3:
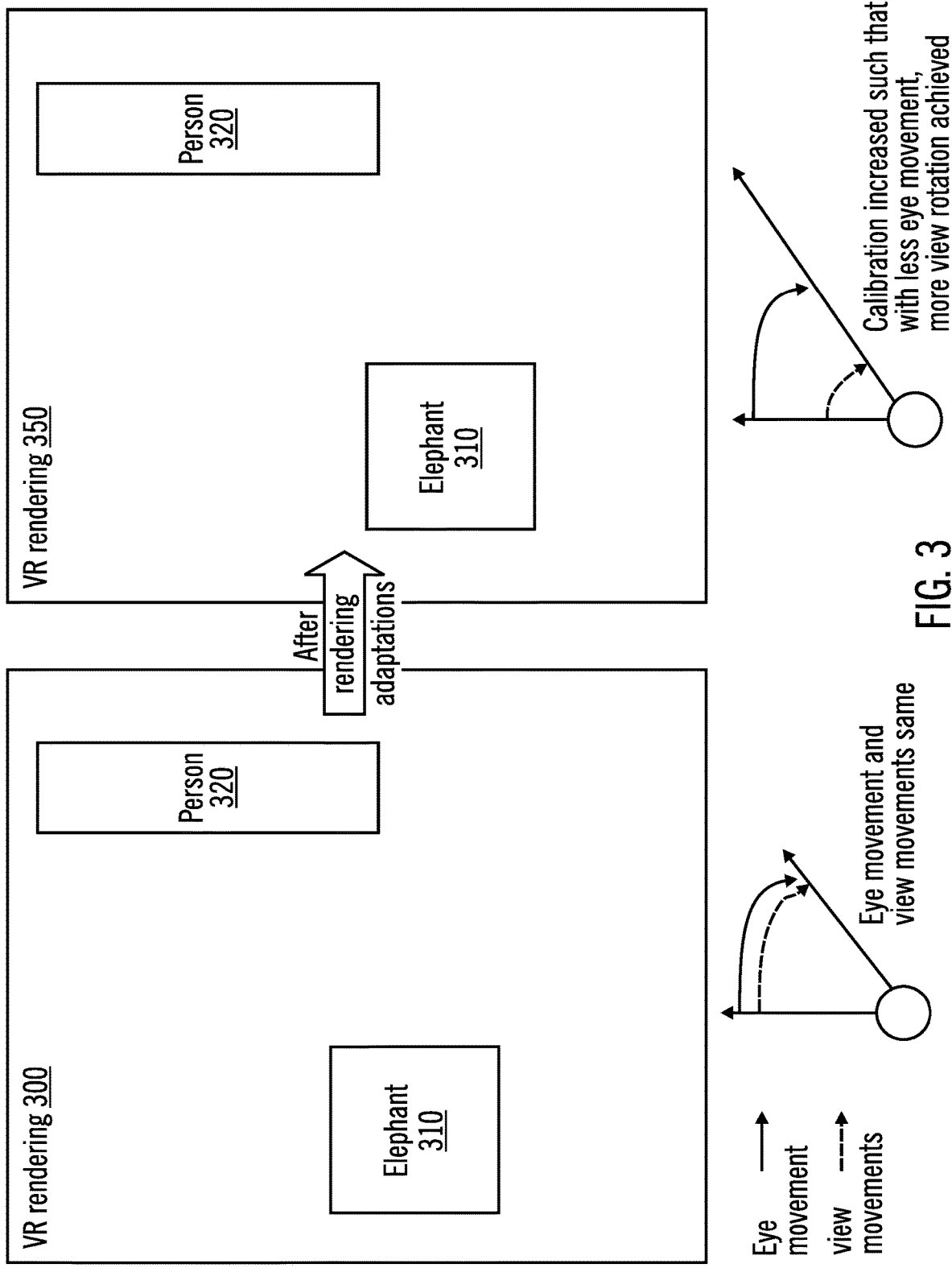
FIG. 3 illustrates rotation movement calibration adaptation in accordance with certain embodiments.

FIG. 3 illustrates rotation movement calibration adaptation in accordance with certain embodiments. Rendition 300 illustrates the VR content before adaptation. Rendition 300 illustrates an elephant 310 and a person 320. The eye movement and view movements are the same for rendition 300. Rendition 350 illustrates the VR content after adaptation. In rendition 350, the UI adaptor 180 has increased the calibration such that, with less eye movement, more view rotation is achieved.

Users find difficulties in viewing objects in extreme corners, which leads to more movement of the eye and/or head towards corners, which could lead to eye stress if head rotations are not noticed. In these cases, the UI adaptor 180 increases the rotation calibration index, which makes the user move eyes and/or head slightly, which may lead to an increased magnitude of rotation.

Figure 4:
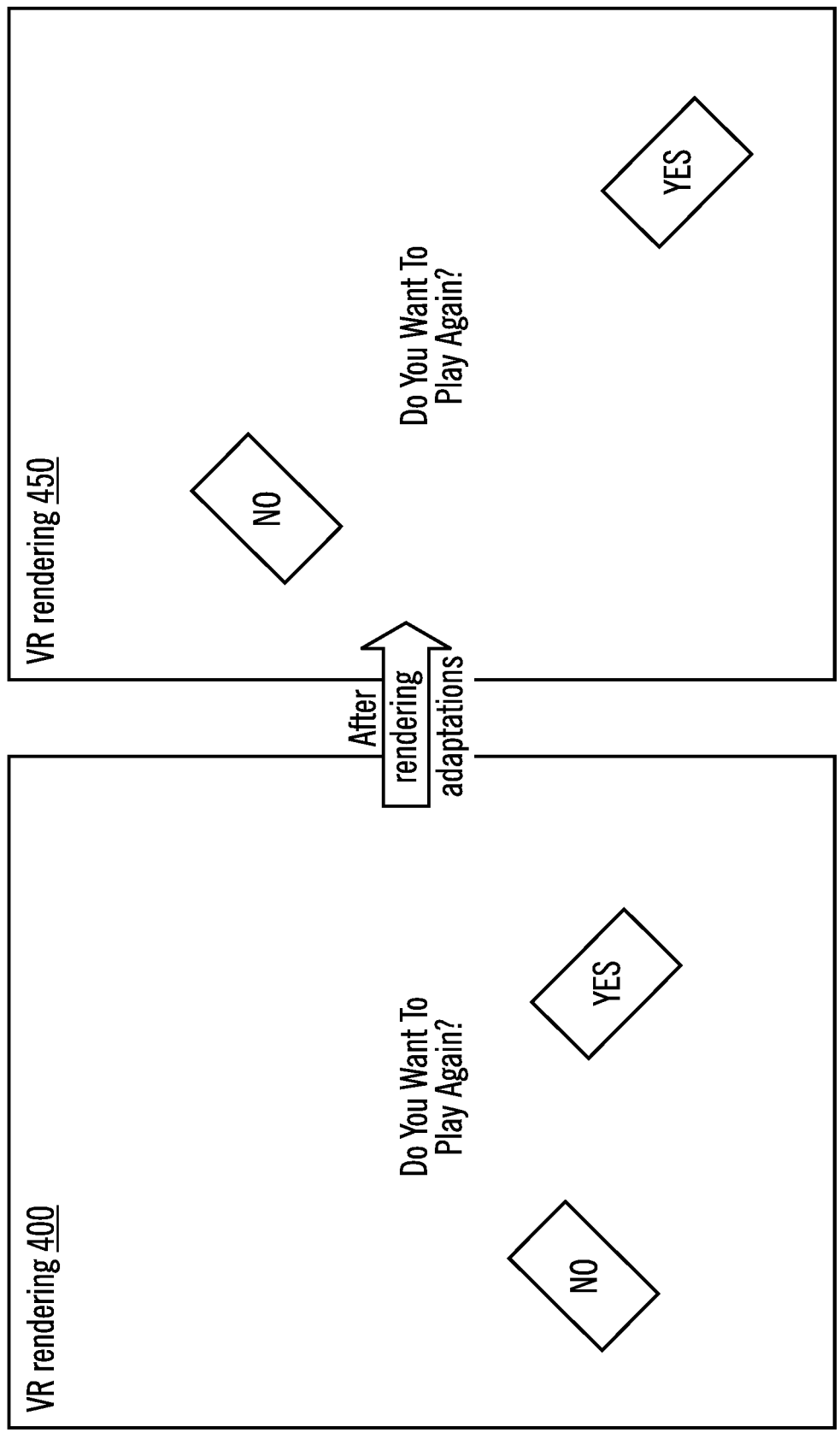
FIG. 4 illustrates UI position adaption in accordance with certain embodiments.

FIG. 4 illustrates UI position adaption in accordance with certain embodiments. Rendition 400 illustrates the VR content before adaptation. In rendition 400, the No and Yes boxes are close to each other. Rendition 450 illustrates the VR content after adaptation. In rendition 450, the No box has been moved (i.e., it's position has been adapted in the UI). In particular, the No and Yes boxes are placed wider apart, leading to move eye wandering.

When the user focus is more static in a defined area, this may lead to eye stress due to same point focus issues. In these contexts, the UI adaptor 180 places user interaction widgets wider apart, leading the user to more eye wandering in the VR space, which avoids same area focus issues.

Figure 5A:
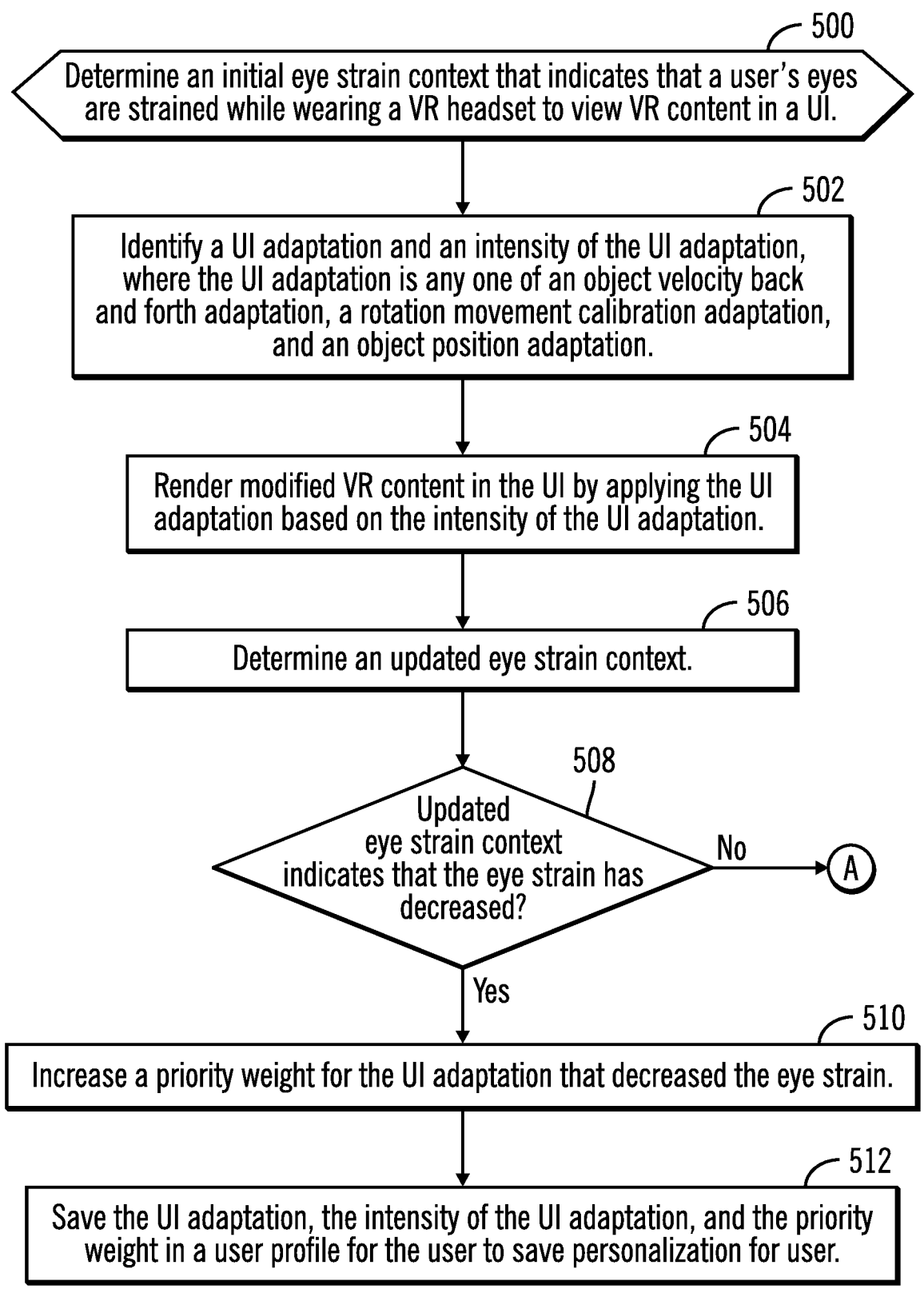
FIGS. 5A and 5B illustrate, in a flowchart, operations for adapting a UI of a VR headset in accordance with certain embodiments.
Figure 5B:
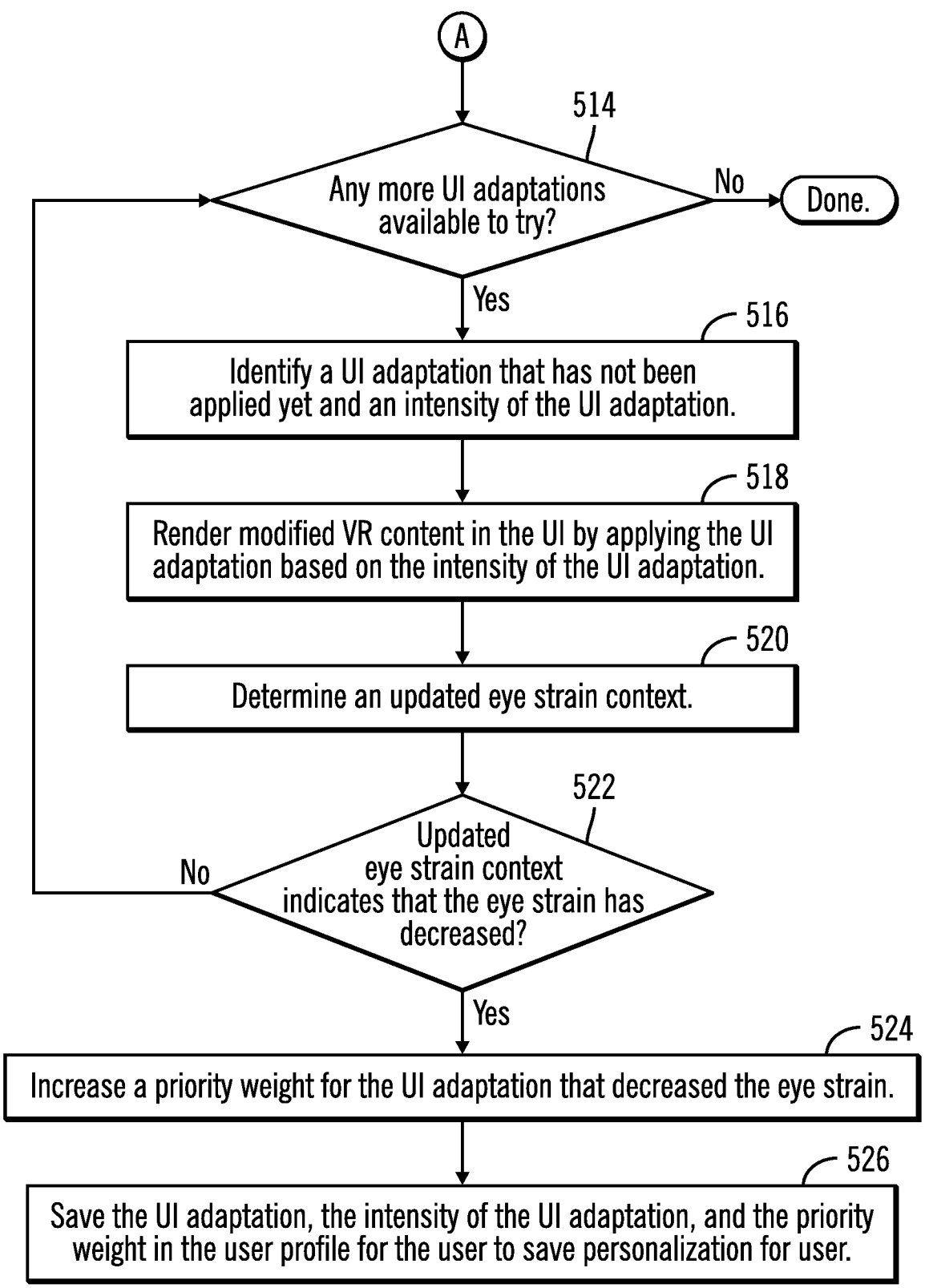

FIGS. 5A and 5B illustrate, in a flowchart, operations for adapting a UI of a VR headset in accordance with certain embodiments. Control begins at block 500 with the UI adaptor 180 determining an initial eye strain context that indicates that the user's eyes are strained while wearing a VR headset to view VR content in a UI.

In block 502, the UI adaptor 180 identifies a UI adaptation and an intensity of the UI adaptation, where the UI adaptation is any one of an object velocity back and forth adaptation, a rotation movement calibration adaptation, and an object position adaptation. In certain embodiments, the UI adaptations are generated based on processing a sensor stream to generate an eye blink rate, iris enlargement, contraction event data, and an eye fatigue index, processing an application on/off time to generate an expected application usage time, processing eye and head interaction events to generate an interaction rate for each UI control.

In block 504, the UI adaptor 180 renders modified VR content in the UI by applying the UI adaptation based on the intensity of the UI adaptation. In certain embodiments, the UI adaptor 180 identifies and applies multiple UI adaptations at one time.

In block 506, the UI adaptor 180 determines an updated eye strain context. In block 508, the UI adaptor 180 determines whether the updated eye strain context indicates that the user's eye strain has decreased (i.e., the user is experiencing less eye strain). If so, processing continues to block 510, otherwise, processing continues to block 514 (FIG. 5B).

In block 510, the UI adaptor 180 increases a priority weight for the UI adaptation that decreased the eye strain (i.e., improved the eye strain). In certain embodiments, the increase in the priority weight reflects how much of an improvement there was in eye strain (e.g., the greater the decrease in eye strain, the higher the priority weight increase). In block 512, the UI adaptor 180 saves the UI adaptation, the intensity of the UI adaptation, and the priority weight in a user profile for the user to save personalization for user.

In block 514, the UI adaptor 180 determines whether there are any more UI adaptations available to try. If so, processing continues to block 516, otherwise, processing is done.

In block 516, the UI adaptor 180 identifies a UI adaptation that has not been applied yet and an intensity of the UI adaptation. In block 518, the UI adaptor 180 renders modified VR content in the UI by applying the UI adaptation based on the intensity of the UI adaptation.

In block 520, the UI adaptor 180 determines an updated eye strain context. In block 522, the UI adaptor 180 determines whether the updated eye strain context indicates that the user's eye strain has decreased (i.e., the user is experiencing less eye strain). If so, processing continues to block 524, otherwise, processing continues to block 514 (FIG. 5B).

In block 524, the UI adaptor 180 increases a priority weight for the UI adaptation that decreased the eye strain (i.e., improved the eye strain). In block 526, the UI adaptor 180 saves the UI adaptation, the intensity of the UI adaptation, and the priority weight in the user profile for the user to save personalization for user.

By iterating through the possible UI adaptations, the UI adaptor 180 determines which of the UI adaptations has a highest positive response from the user, and that UI adaptation is prioritized more than a UI adaptation that has a slight positive response or a negative response form the user. This allows the UI adaptor 180 to later use the user profile to render the UI for the user for a subsequent (e.g., future) use of the VR headset to avoid eye strain. In certain embodiments, when the UI adaptor 180 uses the user profile to render the VR content, the UI adaptor 180 may start by applying the UI adaptation with the highest priority and may then apply the other UI adaptations, in order of priority weights.

Figure 6:
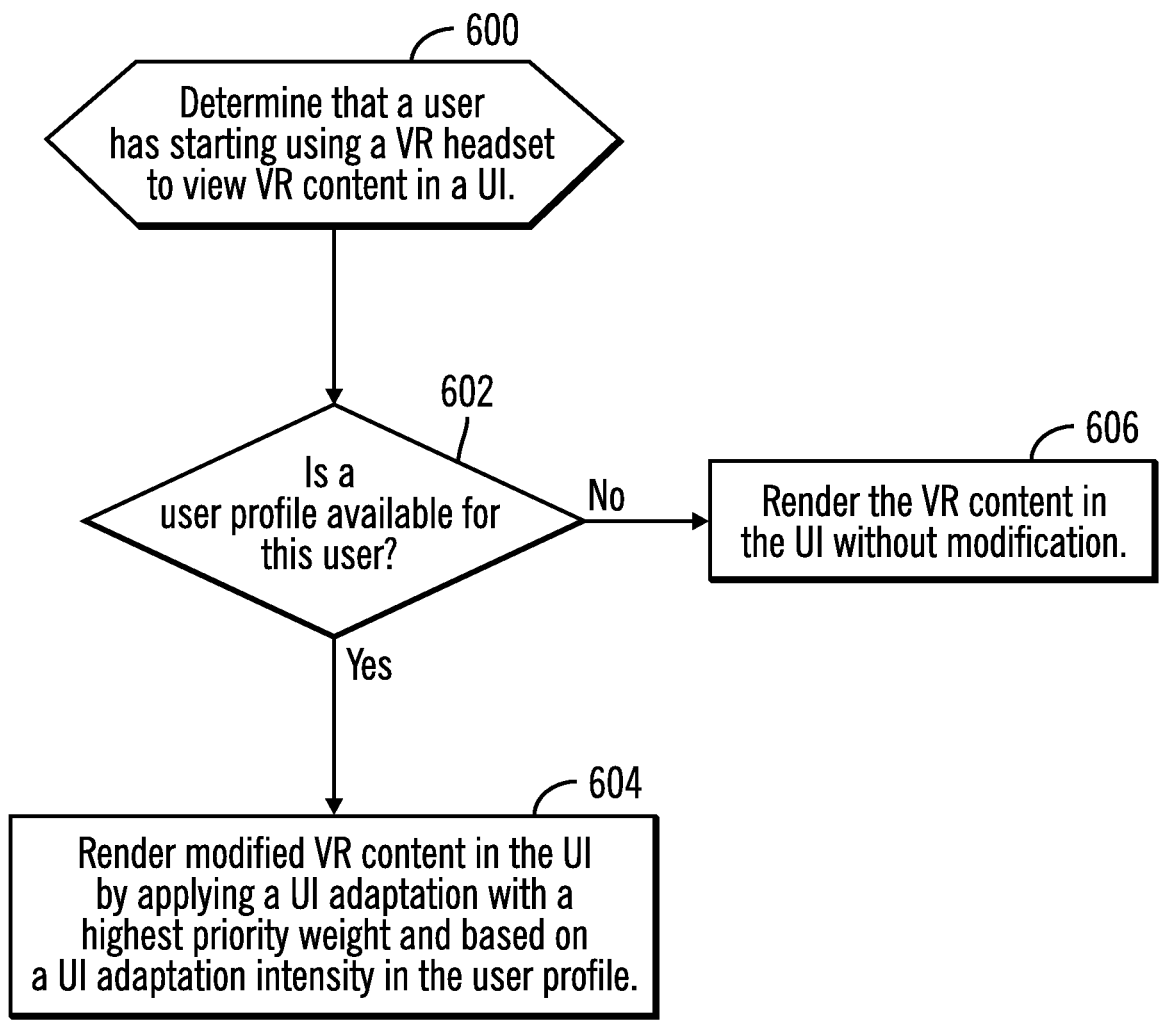
FIG. 6 illustrates, in a flowchart, operations for using a user profile in accordance with certain embodiments.

FIG. 6 illustrates, in a flowchart, operations for using a user profile in accordance with certain embodiments. Control begins at block 600 with the UI adaptor 180 determining that a user has starting using a VR headset to view VR content in a UI. In block 602, the UI adaptor 180 determines whether a user profile is available for this user. If so, processing continues to block 604, otherwise, processing continues to block 606.

In block 604, the UI adaptor 180 renders modified VR content in the UI by applying a UI adaptation with a highest priority weight and based on a UI adaptation intensity in the user profile. The other UI adaptations may then be added as needed (per the processing of FIGS. 5A and 5B). In block 606, the UI adaptor 180 renders the VR content in the UI without modification.

Embodiments may also be used to assess neck strain, headache, etc. and adapt the UI to lessen neck strain, headache, etc. based on input from VR headsets that provide information on the neck and head.

Conventional solutions are focused on data-independent adaptation of the User Interface (UI) and tuning of the VR system. For instance, given a web page, the adaptation of its style has been the focus. Also, conventional solutions do not provide any specific content adaptation solution tailored to a VR environment. Unlike such conventional solutions, embodiments provide data-dependent adaptation of the VR content.

Also, conventional energy/network efficiency solutions thrust an adapted UI upon the user without feedback on whether it is better or not. On the other hand, embodiments use feedback for adaptation of the VR content.

Moreover, conventional solutions evaluate a representative energy efficient UI in user studies, which cannot be generalized for all web pages in the world. However, embodiments may be used with any VR headset and any VR content.

Conventional feedback based techniques do not adapt the UI with the goal of energy efficiency and the feedback is not focused on the effect of adapted UI on user comfort. On the other hand, embodiments adapt the VR content with the goal of energy efficiency and use feedback that is focused on the effect of the adapted VR content on user comfort (e.g., eye strain).

Figure 7:
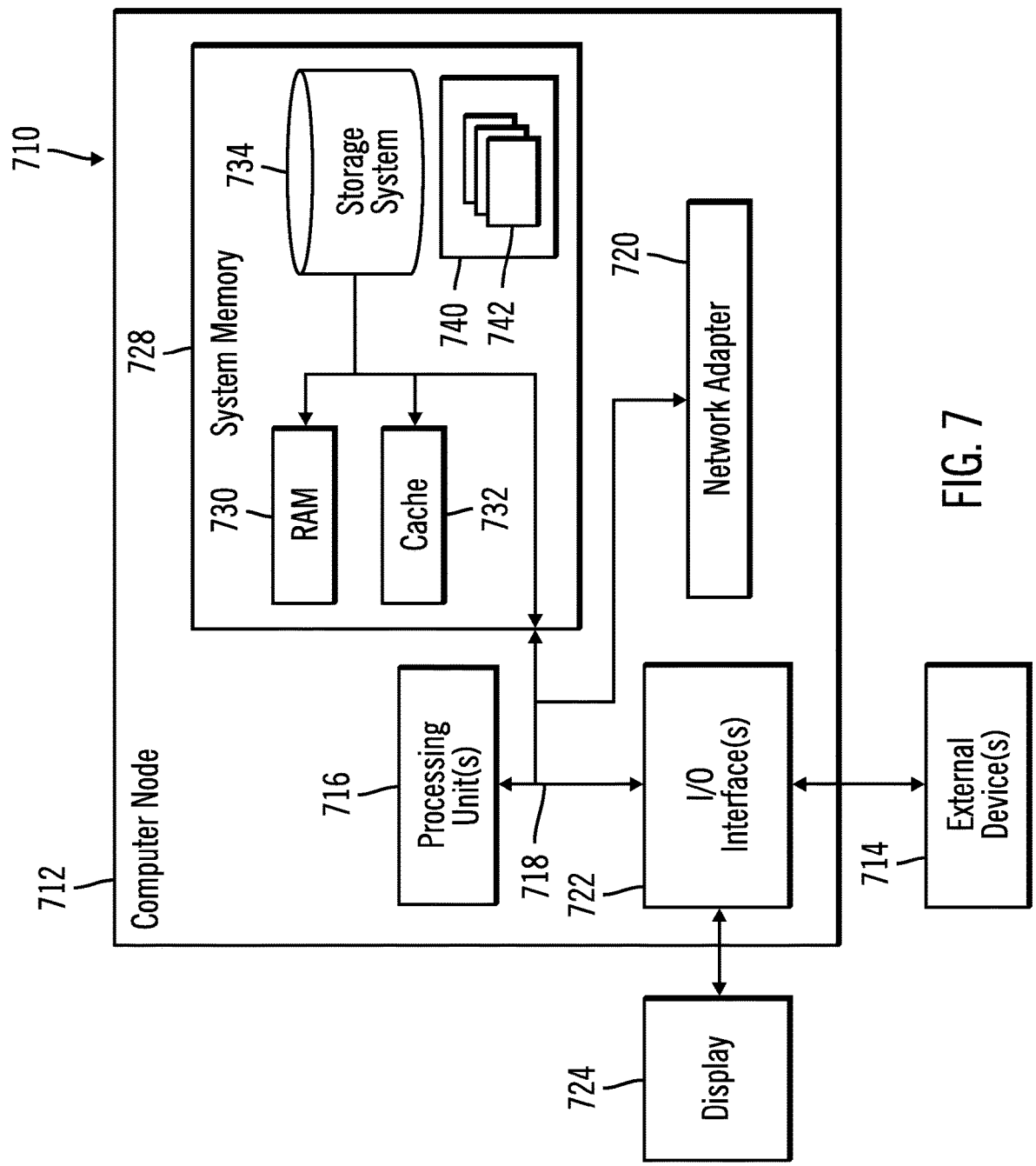
FIG. 7 illustrates a computing node in accordance with certain embodiments.

FIG. 7 illustrates a computing environment 710 in accordance with certain embodiments. Referring to FIG. 7, computer node 712 is only one example of a suitable computing node and is not intended to suggest any limitation as to the scope of use or functionality of embodiments of the invention described herein. Regardless, computer node 712 is capable of being implemented and/or performing any of the functionality set forth hereinabove.

The computer node 712 may be a computer system, which is operational with numerous other general purpose or special purpose computing system environments or configurations. Examples of well-known computing systems, environments, and/or configurations that may be suitable for use with computer node 712 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer node 712 may be described in the general context of computer system executable instructions, such as program modules, being executed by a computer system. Generally, program modules may include routines, programs, objects, components, logic, data structures, and so on that perform particular tasks or implement particular abstract data types. Computer node 712 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer node 712 is shown in the form of a general-purpose computing device. The components of computer node 712 may include, but are not limited to, one or more processors or processing units 716, a system memory 728, and a bus 718 that couples various system components including system memory 728 to one or more processors or processing units 716.

Bus 718 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer node 712 typically includes a variety of computer system readable media. Such media may be any available media that is accessible by computer node 712, and it includes both volatile and non-volatile media, removable and non-removable media.

System memory 728 can include computer system readable media in the form of volatile memory, such as random access memory (RAM) 730 and/or cache memory 732. Computer node 712 may further include other removable/non-removable, volatile/non-volatile computer system storage media. By way of example only, storage system 734 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 718 by one or more data media interfaces. As will be further depicted and described below, system memory 728 may include at least one program product having a set (e.g., at least one) of program modules that are configured to carry out the functions of embodiments of the invention.

Program/utility 740, having a set (at least one) of program modules 742, may be stored in system memory 728 by way of example, and not limitation, as well as an operating system, one or more application programs, other program modules, and program data. Each of the operating system, one or more application programs, other program modules, and program data or some combination thereof, may include an implementation of a networking environment. Program modules 742 generally carry out the functions and/or methodologies of embodiments of the invention as described herein.

Computer node 712 may also communicate with one or more external devices 714 such as a keyboard, a pointing device, a display 724, etc.; one or more devices that enable a user to interact with computer node 712; and/or any devices (e.g., network card, modem, etc.) that enable computer node 712 to communicate with one or more other computing devices. Such communication can occur via Input/Output (I/O) interfaces 722. Still yet, computer node 712 can communicate with one or more networks such as a local area network (LAN), a general wide area network (WAN), and/or a public network (e.g., the Internet) via network adapter 720. As depicted, network adapter 720 communicates with the other components of computer node 712 via bus 718. It should be understood that although not shown, other hardware and/or software components could be used in conjunction with computer node 712. Examples, include, but are not limited to: microcode, device drivers, redundant processing units, external disk drive arrays, RAID systems, tape drives, and data archival storage systems, etc.

In certain embodiments, the computing device 100 has the architecture of computer node 712.

Additional Embodiment Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The foregoing description provides examples of embodiments of the invention, and variations and substitutions may be made in other embodiments.

What is claimed is:

1. A computer-implemented method, comprising:
receiving eye activity data, an application usage time, and an interaction rate for each UI control, wherein the eye activity data comprises an eye fatigue index;
determining an initial eye strain context of a user wearing a Virtual Reality (VR) headset to view VR content in a User Interface (UI) based on the eye activity data;
identifying a UI adaptation and an intensity of the UI adaptation based on the eye activity data, the application usage time, and the interaction rate for each UI control, wherein the UI adaptation is any one or more of an object velocity back and forth adaptation, a rotation movement calibration adaptation, and an object position adaptation;
rendering modified VR content in the UI by applying the UI adaptation based on the intensity of the UI adaptation;
determining an updated eye strain context;
in response to determining that the updated eye strain context indicates that eye strain has decreased,
increasing a priority weight for the UI adaptation; and
saving the UI adaptation, the intensity of the UI adaptation, and the priority weight in a user profile for the user.

2. The computer-implemented method of claim 1, further comprising:
in response to determining that the updated eye strain context indicates that eye strain has not decreased,
identifying a UI adaptation that has not been applied yet and an intensity of the UI adaptation;
rendering modified VR content in the UI by applying the UI adaptation based on the intensity of the UI adaptation;
determining an updated eye strain context;
in response to determining that the updated eye strain context indicates that eye strain has decreased,
increasing a priority weight for the UI adaptation; and
saving the UI adaptation, the intensity of the UI adaptation, and the priority weight in the user profile for the user.

3. The computer-implemented method of claim 1, further comprising:
determining that a user has starting using the VR headset to view the VR content in the UI; and
in response to determining that the user profile is available for the user, rendering modified VR content in the UI by applying a UI adaptation with a highest priority weight and based on a UI adaptation intensity in the user profile.

4. The computer-implemented method of claim 1, further comprising:
determining that a user has starting using the VR headset to view the VR content in the UI; and
in response to determining that the user profile is not available for the user, rendering the VR content in the UI without modification.

5. The computer-implemented method of claim 1, wherein the object velocity back and forth adaptation, the rotation movement calibration adaptation, and the object position adaptation are generated based on:
processing a sensor stream to generate the eye activity data comprising an eye blink rate, iris enlargement, contraction event data, and the eye fatigue index;
processing an application on/off time to generate the application usage time; and
processing eye and head interaction events to generate the interaction rate for each UI control.

6. The computer-implemented method of claim 1, wherein the object velocity back and forth adaptation decreases a velocity of an object in the VR content, wherein the rotation movement calibration adaptation increases a rotation calibration index, and wherein the object position adaptation changes a position of another object in the VR content.

7. A computer program product, the computer program product comprising a computer readable storage medium having program code embodied therewith, the program code executable by at least one processor to perform:
receiving eye activity data, an application usage time, and an interaction rate for each UI control, wherein the eye activity data comprises an eye fatigue index;
determining an initial eye strain context of a user wearing a Virtual Reality (VR) headset to view VR content in a User Interface (UI) based on the eye activity data;
identifying a UI adaptation and an intensity of the UI adaptation based on the eye activity data, the application usage time, and the interaction rate for each UI control, wherein the UI adaptation is any one or more of an object velocity back and forth adaptation, a rotation movement calibration adaptation, and an object position adaptation;
rendering modified VR content in the UI by applying the UI adaptation based on the intensity of the UI adaptation;
determining an updated eye strain context;
in response to determining that the updated eye strain context indicates that eye strain has decreased,
increasing a priority weight for the UI adaptation; and
saving the UI adaptation, the intensity of the UI adaptation, and the priority weight in a user profile for the user.

8. The computer program product of claim 7, wherein the program code is executable by at least one processor to perform:
in response to determining that the updated eye strain context indicates that eye strain has not decreased,
identifying a UI adaptation that has not been applied yet and an intensity of the UI adaptation;
rendering modified VR content in the UI by applying the UI adaptation based on the intensity of the UI adaptation;
determining an updated eye strain context;
in response to determining that the updated eye strain context indicates that eye strain has decreased,
increasing a priority weight for the UI adaptation; and
saving the UI adaptation, the intensity of the UI adaptation, and the priority weight in the user profile for the user.

9. The computer program product of claim 7, wherein the program code is executable by at least one processor to perform:
determining that a user has starting using the VR headset to view the VR content in the UI; and
in response to determining that the user profile is available for the user, rendering modified VR content in the UI by applying a UI adaptation with a highest priority weight and based on a UI adaptation intensity in the user profile.

10. The computer program product of claim 7, wherein the program code is executable by at least one processor to perform:
determining that a user has starting using the VR headset to view the VR content in the UI; and
in response to determining that the user profile is not available for the user, rendering the VR content in the UI without modification.

11. The computer program product of claim 7, wherein the object velocity back and forth adaptation, the rotation movement calibration adaptation, and the object position adaptation are generated based on:
processing a sensor stream to generate the eye activity data comprising an eye blink rate, iris enlargement, contraction event data, and the eye fatigue index;
processing an application on/off time to generate the application usage time; and
processing eye and head interaction events to generate the interaction rate for each UI control.

12. The computer program product of claim 7, wherein the object velocity back and forth adaptation decreases a velocity of an object in the VR content, wherein the rotation movement calibration adaptation increases a rotation calibration index, and wherein the object position adaptation changes a position of another object in the VR content.

13. A computer system, comprising:
one or more processors, one or more computer-readable memories and one or more computer-readable, tangible storage devices; and
program instructions, stored on at least one of the one or more computer-readable, tangible storage devices for execution by at least one of the one or more processors via at least one of the one or more memories, to perform operations comprising:
receiving eye activity data, an application usage time, and an interaction rate for each UI control, wherein the eye activity data comprises an eye fatigue index;
determining an initial eye strain context of a user wearing a Virtual Reality (VR) headset to view VR content in a User Interface (UI) based on the eye activity data;
identifying a UI adaptation and an intensity of the UI adaptation based on the eye activity data, the application usage time, and the interaction rate for each UI control, wherein the UI adaptation is any one or more of an object velocity back and forth adaptation, a rotation movement calibration adaptation, and an object position adaptation;
rendering modified VR content in the UI by applying the UI adaptation based on the intensity of the UI adaptation;
determining an updated eye strain context;
in response to determining that the updated eye strain context indicates that eye strain has decreased,
increasing a priority weight for the UI adaptation; and
saving the UI adaptation, the intensity of the UI adaptation, and the priority weight in a user profile for the user.

14. The computer system of claim 13, wherein the operations further comprise:
in response to determining that the updated eye strain context indicates that eye strain has not decreased,
identifying a UI adaptation that has not been applied yet and an intensity of the UI adaptation;
rendering modified VR content in the UI by applying the UI adaptation based on the intensity of the UI adaptation;
determining an updated eye strain context;
in response to determining that the updated eye strain context indicates that eye strain has decreased,
increasing a priority weight for the UI adaptation; and
saving the UI adaptation, the intensity of the UI adaptation, and the priority weight in the user profile for the user.

15. The computer system of claim 13, wherein the operations further comprise:
determining that a user has starting using the VR headset to view the VR content in the UI; and
in response to determining that the user profile is available for the user, rendering modified VR content in the UI by applying a UI adaptation with a highest priority weight and based on a UI adaptation intensity in the user profile.

16. The computer system of claim 13, further comprising:
determining that a user has starting using the VR headset to view the VR content in the UI; and
in response to determining that the user profile is not available for the user, rendering the VR content in the UI without modification.

17. The computer system of claim 13, wherein the object velocity back and forth adaptation, the rotation movement calibration adaptation, and the object position adaptation are generated based on:
processing a sensor stream to generate the eye activity data comprising an eye blink rate, iris enlargement, contraction event data, and the eye fatigue index;
processing an application on/off time to generate the application usage time; and
processing eye and head interaction events to generate the interaction rate for each UI control.

18. The computer system of claim 13, wherein the object velocity back and forth adaptation decreases a velocity of an object in the VR content, wherein the rotation movement calibration adaptation increases a rotation calibration index, and wherein the object position adaptation changes a position of another object in the VR content.

* * * * *